United States Patent [19]

Walker et al.

[11] 4,240,960

[45] Dec. 23, 1980

[54] TRIMETHYLSILYL SUBSTITUTED PENICILLINS

[75] Inventors: Derek Walker, Jamesville; Herbert H. Silvestri, Dewitt; Chester Sapino, East Syracuse; David A. Johnson, Fayetteville, all of N.Y.

[73] Assignee: Bristol-Myers Company, New York, N.Y.

[21] Appl. No.: 21,852

[22] Filed: Mar. 19, 1979

Related U.S. Application Data

[63] Continuation-in-part of Ser. No. 4,780, Jan. 19, 1979, abandoned, which is a continuation-in-part of Ser. No. 970,704, Dec. 18, 1978, abandoned.

[51] Int. Cl.$^3$ .......................................... C07D 499/32
[52] U.S. Cl. ................................................. 260/239.1
[58] Field of Search ..................................... 260/239.1

[56] References Cited

U.S. PATENT DOCUMENTS

| | | | |
|---|---|---|---|
| 2,985,648 | 5/1961 | Doyle et al. | 260/239.1 |
| 3,008,956 | 11/1961 | Nettleton et al. | 260/239.1 |
| 3,180,862 | 4/1965 | Silvestri et al. | 260/239.1 |
| 3,192,198 | 6/1965 | Nayler et al. | 260/239.1 |
| 3,198,804 | 8/1965 | Johnson et al. | 260/306.7 |
| 3,249,622 | 5/1966 | Herrling et al. | 260/306.7 |
| 3,271,389 | 9/1966 | Johnson et al. | 260/239.1 |
| 3,478,018 | 11/1969 | Robinson et al. | 260/239.1 |
| 3,479,338 | 11/1969 | Adams | 260/239.1 |
| 3,487,073 | 12/1969 | Adams et al. | 260/239.1 |
| 3,499,909 | 3/1970 | Weissenburger et al. | 260/306.7 |
| 3,595,855 | 7/1971 | Robinson | 260/239.1 |
| 3,654,266 | 4/1972 | Robinson | 260/239.1 |
| 3,674,776 | 7/1972 | Long et al. | 260/239.1 |
| 3,912,719 | 10/1975 | Sapino et al. | 260/239.1 |
| 3,980,637 | 9/1976 | Grossman et al. | 260/239.1 |
| 4,128,547 | 12/1978 | van der Drift et al. | 260/239.1 |

FOREIGN PATENT DOCUMENTS

| | | | |
|---|---|---|---|
| 938321 | 10/1963 | United Kingdom | 260/239.1 |
| 958853 | 6/1964 | United Kingdom | 260/239.1 |
| 962719 | 7/1964 | United Kingdom | 260/239.1 |
| 1008468 | 10/1965 | United Kingdom | 260/239.1 |
| 1339605 | 12/1973 | United Kingdom | 260/239.1 |

*Primary Examiner*—Natalie Trousof
*Assistant Examiner*—Vera C. Clarke
*Attorney, Agent, or Firm*—Herbert W. Taylor, Jr.

[57] ABSTRACT

Trimethylsilyl or another easily hydrolyzed ester of 6-trimethylsilyloxycarbonylaminopenicillanic acid was prepared by bubbling dry carbon dioxide into an anhydrous solution of the corresponding 6-trimethylsilylaminopenicillanate and found to be a useful intermediate in the production of penicillins, e.g., amoxicillin and ampicillin, by its acylation in anhydrous media with the appropriate acid chloride or acid chloride hydrochloride.

8 Claims, No Drawings

TRIMETHYLSILYL SUBSTITUTED PENICILLINS

CROSS-REFERENCE TO RELATED APPLICATIONS

This application is a continuation-in-part of our prior, copending application Ser. No. 4,780 filed Jan. 19, 1979, now abandoned, which in turn was a continuation-in-part of our prior, copending application Ser. No. 970,704 filed Dec. 18, 1978, and now abandoned.

BACKGROUND OF THE INVENTION

1. Field of the Invention

The process of the present invention produces an antibacterial agent of the class commonly called semi-synthetic penicillins and, preferably, of the subclass characterized by an α-amino group on the acyl sidechain at the 6-position as in ampicillin and amoxicillin.

2. Description of the Prior Art

The first commercial penicillin having an α-amino group on the 6-acylamido sidechain was ampicillin, which is 6-(D-α-amino-α-phenylacetamido)penicillanic acid (see U.S. Pat. No. 2,985,648).

Amoxicillin is an antibacterial agent used in human therapy and marketed as the trihydrate of the free acid (i.e., the zwitterion). It is described, for example, in J. Chem. Soc. (London), pages 1920–1922 (1971) and Antimicrobial Agents and Chemotherapy-1970, pages 407–430 (1971) and in U.S. Pat. No. 3,674,776 (see also U.S. Pat. No. 3,192,198). Its chemical name is 6-[D-α-amino-α-(p-hydroxyphenyl)acetamido]penicillanic acid.

The use of amino acid chloride hydrochlorides to make such penicillins was disclosed in the patent literature, e.g. in U.K. Pat. No. 938,321 and U.K. Pat. No. 959,853 under anhydrous conditions (the latter utilized the protection during acylation of the carboxyl group of the 6-aminopenicillanic acid with a silyl group as was also disclosed in U.K. Pat. No. 1,008,468 and U.S. Pat. No. 3,249,622) and in U.K. Pat. No. 962,719 in cold aqueous acetone. These penicillins are amphoteric amino acids and use was therefore made in their isolation (e.g. as disclosed in U.S. Pat. No. 3,157,640 and U.S. Pat. No. 3,271,389) of certain aliphatic unsymmetrical branched chain secondary amines (often called liquid amine resins) which had previously been used in the isolation of 6-aminopenicillanic acid which is also an amphoteric amino acid (see U.S. Pat. No. 3,008,956). Improved methods of isolating and purifying such penicillins were disclosed, e.g. in U.S. Pat. No. 3,180,862 via β-naphthalene sulfonates and in U.S. Pat. No. 3,198,804 via intermediate isolation and subsequent facile hydrolysis of hetacillin.

The use of a silyl group to protect the carboxyl group of a natural penicillin during chemical cleavage to 6-aminopenicillanic acid was disclosed in U.S. Pat. No. 3,499,909. The use of silylated 6-aminopenicillanic acid during anhydrous acylation with amino acid chloride hydrochlorides was disclosed in numerous patents, e.g. U.S. Pat. No. 3,479,018; U.S. Pat. No. 3,595,855; U.S. Pat. No. 3,654,266; U.S. Pat. No. 3,479,338 and U.S. Pat. No. 3,487,073. Some of these patents also disclose use of liquid amine resins. See also U.S. Pat. Nos. 3,912,719, 3,980,637 and 4,128,547.

U.K. Pat. No. 1,339,605 contains various specific and detailed examples for preparing amoxicillin by the reaction of a silylated derivative of 6-aminopenicillanic acid with a reactive derivative (including the chloride hydrochloride) of D-(-)-α-amino-p-hydroxyphenylacetic acid in which the amino group is protected, thereafter removing the silyl group(s) by hydrolysis or alcoholysis and thereafter, when possible, recovering the amoxicillin, usually as the crystalline trihydrate. Thus crystalline amoxicillin was obtained in Example 1 by isoelectric precipitation from an aqueous solution, e.g. at pH 4.7. Purification was presumably achieved by this example by dissolving the crude product (before isoelectric precipitation) in water at an acidic pH such as 1.0 (e.g. in aqueous hydrochloric acid) in the presence of a water-immiscible organic solvent such as methyl isobutyl ketone (4-methylpentan-2-one). Much the same procedure was used in U.S. Pat. No. 3,674,776.

A search of Chemical Abstracts Formula Indexes Vols. 58–87 showed that I had not been indexed.

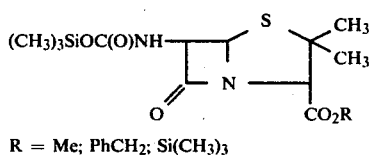

R = Me; PhCH$_2$; Si(CH$_3$)$_3$

Siloxycarbonylamino derivatives are indexed under silanol, carbamic acid and under N-carboxy derivatives of compounds as the trimethylsilyl ester.

However, the following papers appear of some interest:

1. Breederveld, H.: The interaction of dialkylaminosilanes with carbon disulphide. A novel reaction in organosilicon chemistry. Recueil, 79, 1126 (1960).

2. Cragg, R. H.; Lappert, M. F.: Amino-derivatives of metals and metalloids. Part IV. Aminosilylation and aminophosphination of some unsaturated substrates. J. Chem. Soc. (A), 82–85 (1966).

3. Kricheldorf, H. R.: Herstellung von N-Silyloxycarbonylaminosaure-derivaten. Synthesis, 259–60 (1970)(Ger.); C.A. 73, 45820r (1970).

4. Kricheldorf, H. R.: The preparation of amino acid N-carboxyanhydrides (NCAs) from N-siloxycarbonyl amino acid trimethylsilyl esters. Chem. Ber., 104, 87–91 (1971)(Ger.); C.A. 74, 54156b (1971).

5. Mironov, V. F.; Kozyukov, V. P.; Kirilin, A. D., et al.: Synthesis and reactions of silyl carbamates. New method for the preparation of organic isocyanates without the use of phosgene. Zn Obshch Khim, 45, 1971–73, (1975).

6. Sheludyakov, V. D.; Kirilin, A. D.; Mironov, V. F.: New Method for the preparation of (carbamoyloxy)-silanes. Zh Obshch Khim, 45, 471 (1975).

7. Mironov, V. F.; Sheludyakov, V. D.; Kirilin, A. D.: Siloxycarbonylation of amines. Zh Obshch Khim, 46, 2297–98 (1976).

8. Farbenfabriken Bayer A-G (Oertel, G., et al.): Organosilicon compounds. Chem. Abs., 60, 6868b. (Ger. Offen. No. 1,157,226).

SUMMARY OF THE INVENTION

There is provided by the present invention the process for the production of a conventional penicillin which comprises reacting a compound of the formula

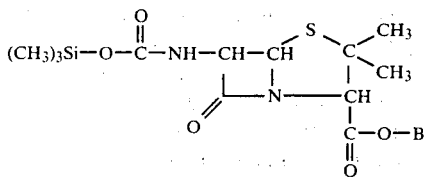

wherein B is an easily cleavable ester protecting group selected from the group consisting of trimethylsilyl, benzhydryl, benzyl, p-nitrobenzyl, p-methoxybenzyl, trichloroethyl, phenacyl, acetonyl, methoxymethyl, 5-indanyl, 3-phthalidyl, 1-[(ethoxycarbonyl)oxy]ethyl, pivaloyloxymethyl and acetoxymethyl in an anhydrous inert organic solvent and preferably in methylene chloride, preferably in the presence of a weak base which is preferably propylene oxide and preferably at a temperature above −10° C., and more preferably in the range of −8° C. to 20° C., and more preferably in the range of 0° C. to 20° C. and most preferably of approximately 20° C., with approximately an equimolar weight of an acid chloride or chloride hydrochloride with the latter being preferably added in portions to the solution of the former, and then, if desired, converting group B to hydrogen.

A conventional penicillin as defined herein is one which has been described previously in the patent or scientific literature, including abstracts thereof.

There is also provided, according to the present invention, the process for the production of the compound of the formula

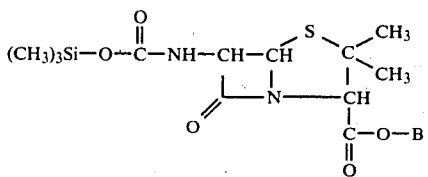

wherein B is an easily cleavable ester protecting group selected from the group consisting of trimethylsilyl, benzhydryl, benzyl, p-nitrobenzyl, p-methoxybenzyl, trichloroethyl, phenacyl, acetonyl, methoxymethyl, 5-indanyl, 3-phthalidyl, 1-[(ethoxycarbonyl)oxy]ethyl, pivaloyloxymethyl and acetoxymethyl which comprises adding dry carbon dioxide as a gas to a solution of a compound having the formula

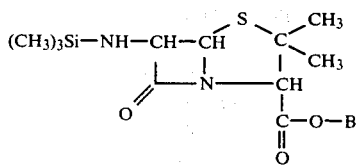

wherein B has the same meaning as above, in an anhydrous inert organic solvent, preferably methylene chloride, at room temperature or at a temperature in the range of 0° C. to 100° C. until completion of the reaction.

There is further provided as a preferred embodiment of the present invention the process for the production of a 6-α-aminoarylacetamidopenicillanic acid, preferably ampicillin or amoxicillin, which comprises reacting a compound of the formula

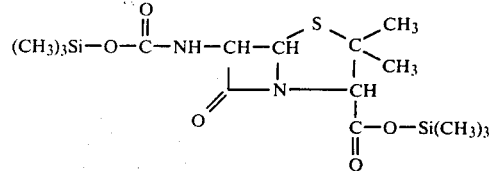

in an anhydrous inert organic solvent and preferably in methylene chloride, preferably in the presence of a weak base which is preferably propylene oxide and preferably at a temperature above −10° C., and more preferably in the range of −8° C. to 20° C., and more preferably in the range of 0° C. to 20° C. and most preferably of approximately 20° C., with approximately an equimolar weight of a D-(-)-α-aminoarylacetyl chloride hydrochloride, preferably D-(-)-2-phenylglycyl chloride hydrochloride or D-(-)-2-p-hydroxyphenylglycyl chloride hydrochloride respectively, with the latter being preferably added in portions to the solution of the former.

One of the surprising features of the new process is the stability of the anhydrous acylation solution. This can be held for long periods of time even at room temperature without noticeable decomposition of the penicillin molecule. This is in contrast to the behavior of acylation solutions in heretofore described processes. This stability advantage allows us to carry out the acylation reaction at much higher temperatures (we used room temperature) than are normally employed in ampicillin manufacture which are normally less than 0° C. and typically about −10° C.

There is also provided as a preferred embodiment, the process for the production of the compound of the formula

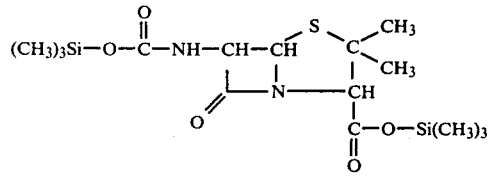

which comprises adding dry carbon dioxide as a gas to a solution of trimethylsilyl 6-trimethylsilylaminopenicillanate in an anhydrous inert organic solvent, preferably methylene chloride, at room temperature or at a temperature in the range of 0° C. to 100° C. until completion of the reaction.

There is further provided as a preferred embodiment the compound having the formula

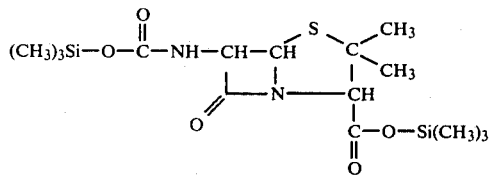

This compound is referred to herein by various trivial names such as bis silylated carbamate of 6-APA, SCA, 6-trimethylsilyloxycarbonylpenicillanic TMS ester and TMSO₂C.APA.TMS.

The very existence of this compound is surprising in view of the well-known fact that reaction of 6-APA with carbon dioxide destroys the 6-APA and produces 8-hydroxypenillic acid as disclosed, for example, in U.S. Pat. No. 3,225,033.

A key to obtaining quantitative yields of 6-trimethylsilyloxycarbonylaminopenicillanic acid trimethyl silyl ester (TMSO₂C.APA.TMS) lies in completely producing the 6-APA bis TMS precursor in the first instance. This has been achieved by reacting 6-APA with hexamethyldisilazane (HMDS) as in the following schematic outline:

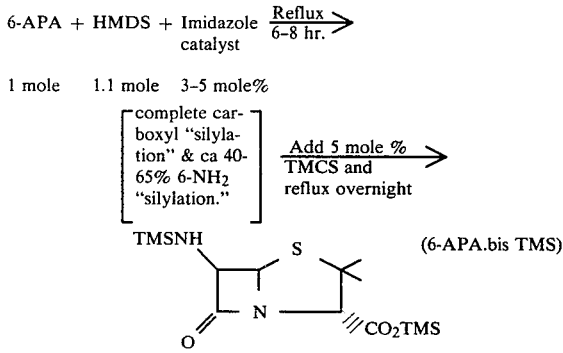

Completion of the bis trimethylsilylation reaction can be readily followed using NMR. The 3-trimethylsilyloxycarbonyl group shows a methylsilyl singlet at 0.31 ppm (tetramethylsilane=0) while the 6-trimethylsilylamine group shows a methylsilyl singlet at 0.09 ppm.

The 6-APA trimethylsilylation reaction has so far only been carried out in methylene chloride. However, other solvents may be used, e.g. acetonitrile, dimethylformamide or even HMDS itself.

Conversion of the trimethylsilylamino group to the trimethylsilyloxycarbonylamino group is readily achieved by bubbling dry $CO_2$ into the reaction solution. The conversion is easily followed by NMR because the trimethylsilylamino singlet at 0.09 ppm declines as a new singlet for the trimethylsilyloxycarbonylamino group appears at 0.27 ppm.

When the process of the present invention is used to produce ampicillin, ampicillin anhydrate, ampicillin trihydrate, amoxicillin and amoxicillin trihydrate the final products are isolated and purified according to conventional methods well-known in the art as illustrated by the disclosures of U.S. Pat. Nos. 3,912,719, 3,980,637 and 4,128,547 and that of other patents and publications cited therein.

Illustrative Preparations of Reagents

The acid chlorides used in the examples below can be replaced by a variety of other acid chlorides to produce conventional penicillins.

Thus the acyl halide may be chosen to introduce any desired acyl group at the 6-amino position as is well known in the art, e.g. U.S. Pat. No. 3,741,959. It is thus possible to introduce specific acyl radicals including, but not limited to, those defined in the following general formulae:

(i) $R^u C_n H_{2n} CO-$ where $R^u$ is aryl (carboxylic or heterocyclic), cycloalkyl, substituted aryl, substituted cycloalkyl, or a non-aromatic or mesoionic heterocyclic group, and n is an integer from 1-4. Examples of this group include phenylacetyl, substituted phenylacetyl. e.g. fluorophenylacetyl, nitrophenylacetyl, aminophenylacetyl, acetoxyphenylacetyl, methoxyphenylacetyl, methphenylacetyl, or hydroxyphenylacetyl; N,N-bis(2-chloroethyl)aminophenylpropionyl; thien-3- and -3-acetyl; 4-isoxazolyl and substituted 4-isoxazolylacetyl; pyridylacetyl; tetrazolylacetyl or a sydnoneacetyl group. The substituted 4-isoxazolyl group may be a 3-aryl-5-methyl isoxazol-4-yl group, the aryl group being, e.g. phenyl or halophenyl, e.g. chloro- or bromophenyl. An acyl group of this type is 3-o-chlorophenyl-5-methyl isoxazol-4-yl-acetyl.

(ii) $C_n H_{2n+1} CO-$ where n is an integer from 1-7. The alkyl group may be straight or branched, and if desired, may be interrupted by an oxygen or sulphur atom or substituted by, e.g. a cyano group. Examples of such groups include cyanoacetyl, hexanoyl, heptanoyl, octanoyl and butylthioacetyl.

(iii) $C_n H_{2n-1} CO-$ where n is an integer from 2-7. The group may be straight or branched and, if desired, may be interrupted by an oxygen or a sulphur atom. An example of such a group is allylthioacetyl.

(iv)

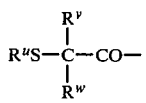

where $R^u$ has the meaning defined under (i) and in addition may be benzyl, and $R^v$ and $R^w$ which may be the same or different each represent hydrogen, phenyl, benzyl, phenethyl or lower alkyl. Examples of such groups include phenoxyacetyl, 2-phenoxy-2-phenylacetyl, 2-phenoxypropionyl, 2-phenoxybutyryl, benzyloxycarbonyl, 2-methyl-2-phenxypropionyl, p-cresoxyacetyl and p-methylthiophenoxyacetyl.

(v)

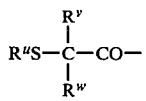

where $R^u$ has the meaning defined under (i) and, in addition, may be benzyl and $R^v$ and $R^w$ have the meanings defined under (iv). Examples of such groups include S-phenylthioacetyl, S-chlorophenylthioacetyl, S-fluorophenylthioacetyl, pyridylthioacetyl, and S-benzylthioacetyl.

(vi) $R^u Z(CH_2)_m CO-$ where $R^u$ has the meaning defined under (i) and, in addition, may be benzyl, Z is an oxygen or sulphur atom and m is an integer from 2-5. An example of such a group is S-benzylthiopropionyl.

(vii) $R^u CO-$ where $R^u$ has the meaning defined under (i). Examples of such groups include benzoyl, substituted benzoyl (e.g. aminobenzoyl), 4-isoxazolyl- and substituted 4-isoxazolyl carbonyl, cyclopentanecarbonyl, sydone carbonyl, naphthoyl and substituted naphthoyl (e.g. 2-ethoxynapthoyl) quinoxalinylcarbonyl and substituted quinoxalinylcarbonyl (e.g. 3-carboxy-2-quinoxalinylcarbonyl). Other possible substituents for benzoyl include alkyl, alkoxy, phenyl or phenyl substituted with carboxy, alkylamido, cycloalkylamido, allylamido, phenyl(lower)alkylamido, morpholinocarbonyl, pyrrolidinocarbonyl, piperidinocarbonyl, tetrahydropyridino, furfurylamido or N-alkyl-N-anilino, or derivatives thereof, and such substituents may be in the 2- or 2- and 6-positions. Examples of such substituted benzoyl groups are 2,6-dimethoxybenzoyl, 2-biphenylcarbonyl, 2-methylamidobenzoyl and 2-carboxybenzoyl. Where the group $R^u$ represents a substituted 4-isoxazolyl group, the substituents may be as set out above under (i). Examples of such 4-isoxazol groups are 3-phenyl-5-methylisoxazol-4-yl carbonyl, 3-o-chlorophenyl-5-methyl isoxazol-4-yl carbonyl and 3-(2,6-dichlorophenyl)-5-methylisoxazol-4-yl carbonyl.

(viii)

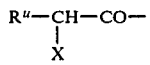

where $R^u$ has the meaning defined under (i) and X is amino, substituted amino (e.g. acylamido or a group obtained by reacting the amino group and/or group(s) of the 7-sidechain with an aldehyde or ketone, e.g. acetone, methylethylketone or ethyl acetoacetate), hydroxy, carboxy, esterified carboxy, triazolyl, tetrazolyl, cyano, halogeno, acyloxy, (e.g. formyloxy or lower alkanoyloxy) or etherified hydroxy group. Examples of such acyl groups are α-aminophenylacetyl, α-carboxyphenylacetyl and 2,2-dimethyl-5-oxo-4-phenyl-1-imidazolidinyl.

(ix)

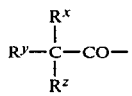

where $R^x$, $R^y$ and $R^z$ which may be the same or different may each represent lower alkyl, phenyl or substituted phenyl. An example of such an acyl group is triphenylcarbonyl.

(x)

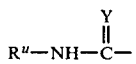

where $R^u$ has the meaning defined under (i) and in addition may be hydrogen, lower alkyl or halogen substituted lower alkyl, and Y represents oxygen or sulphur. An example of such a group is $Cl(CH_2)_2NHCO$.

(xi)

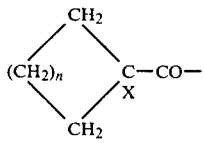

where X has the meaning defined under (viii) above and n is an integer of from 1 to 4. An example of such an acyl group is 1-amino-cyclohexanecarbonyl.

(xii) Amino acyl, for example $R^wCH(NH_2).(CH_2)_nCO$ where n is an integer from 1-10, or $NH_2.C_nH_{2n}Ar(CH_2)_mCO$, where m is zero or an integer from 1-10, and n is 0, 1 or 2, $R^w$ is a hydrogen atom or an alkyl, aralkyl or carboxy group or a group as defined under $R^u$ above, and Ar is an arylene group, e.g. p-phenylene or 1,4-naphthylene. Examples of such groups are disclosed in British patent specification No. 1,054,806. A group of this type is the p-aminophenylacetyl group.

Other acyl groups of this type include those, e.g. δ-aminoadipoyl derived from naturally occurring amino acids and derivatives thereof, e.g. N-benzoyl-δ aminodipoyl.

(xiii) Substituted glyoxylyl groups of the formula $R^y.CO.CO$— where $R^y$ is an aliphatic, araliphatic or aromatic group, e.g. a thienyl group, a phenyl group, or a mono-, di- or tri-substituted phenyl group, the substituents being, for example, one or more halogen atoms (F, Cl, Br, or I), methoxy groups, methyl groups, or amino groups, or a fused benzene ring.

When the acyl group being introduced contains an amino group it may be necessary to protect this during the various reaction stages. The protecting group is conveniently one which can be removed by hydrolysis without affecting the rest of the molecule, especially the lactam and 7-amido linkages. The amine protecting group and the esterifying group at the 4—COOH position can be removed using the same reagent. An advantageous procedure is to remove both groups at the last stage in the sequence. Protected amine groups include urethane, arylmethyl (e.g. trityl) amino, arylmethyleneamino, sulphenylamino or enamine types. Enamine blocking groups are particularly useful in the case of o-aminomethylphenyl acetic acid. Such groups can in general be removed by one or more reagents selected from dilute mineral acids, e.g. dilute hydrochloric acid, concentrated organic acids, e.g. concentrated acetic acid, trifluoroacetic acid, and liquid hydrogen bromide at very low temperatures, e.g. $-80°$ C. A convenient protecting group is the t-butoxycarbonyl group, which is readily removed by hydrolysis with dilute mineral acid, e.g. dilute hydrochloric acid, or preferably with a strong organic acid (e.g. formic acid or trifluoroacetic acid) e.g. at a temperature of $0°$-$40°$ C., preferably at room temperature ($15°$-$25°$ C.). Another convenient protecting group is the 2,2,2-trichloroethoxycarbonyl group which may be split off by an agent such as zinc/acetic acid, zinc/formic acid, zinc/lower alcohols or zinc/pyridine.

The $NH_2$ group may also be protected as $NH_3^+$ by using the amino acid halide as an acid addition salt under conditions in which the amino group remains protonated.

The acid used to form the acid addition salt is preferably one having a $pK_a$ (in water at $25°$ C.) of $\not> x+1$, where x is the $pK_a$ value (in water at $25°$ C.) of the carboxy groups of the amino acid; the acid is preferably monohydric. In practice the acid HQ (see below) will generally have a $pK_a < 3$, preferably $<1$.

Particularly advantageous results have been found to accrue from the process according to the invention when the acyl halide is a salt of an amino acid halide. Amino acid halides have the formula

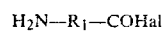

wherein $R_1$ is a divalent organic group and Hal is chloride or bromide. Salts of such amino acid halides have the formula

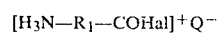

wherein $R_1$ and Hal have the above defined meanings and $Q^-$ is the anion of the acid, HQ having a $pK_a$ as defined above. The acid HQ is preferably a strong mineral acid such as, for example, a hydrohalic acid such as hydrochloric acid or hydrobromic acid. An important amino acid halide, by reason of the valuable penicillin antibiotics which contain the group derived therefrom is D-N-(α-chlorocarbonyl-α-phenyl)methylammonium chloride, D-[PhCH(NH$_3$)COCl]$^+$Cl$^-$, which is referred to herein as D-α-phenylglycylchloride hydrochloride for convenience.

Penicillins obtained by the process according to the invention and having the acylamido group R$^u$CH(NH$_2$)CONH— where R$^u$ has the above-defined meaning, may be reacted with a ketone R$^2$.R$^3$CO where R$^2$ and R$^3$ are lower alkyl groups (C$_1$–C$_4$), to yield compounds believed to contain the group:

$$R^u-CH\underset{HN}{\overset{CO}{\diagdown}}\underset{\underset{R^3}{|}}{\overset{}{N-}}-R^2$$

Compounds of this type include hetacillin, sarpicillin, p-hydroxyhetacillin and sarmoxicillin.

Also included herein and incorporated in full by reference are the acyl groups set forth in U.S. Pat. No. 4,013,648 in columns 7–20 inclusive.

When the acylation process of the present invention is used to produce penicillins the final products are isolated and purified according to conventional methods well-known in the art.

Preferred acyl chlorides used in the present invention to acylate a compound having the formula $$(CH_3)_3Si-O-\overset{O}{\underset{\|}{C}}-NH-\cdots$$

wherein A is (CH$_3$)$_3$Si— or an easily cleavable ester protecting group including the following:

$$A-CH_2\overset{O}{\underset{\|}{C}}-Cl \quad (a)$$

wherein A represents

[structures with CH$_2$NHR' on substituted phenyl, cyclohexadiene, and thiophene]

wherein R is hydrogen, hydroxy or methoxy and R' is hydrogen or methyl and the amino group is blocked, if desired, by conventional blocking groups including particularly by protonation;

$$B-\underset{\underset{NH_2}{|}}{CH}-\overset{O}{\underset{\|}{C}}-Cl \cdot HCl \quad (b)$$

wherein B represents

[structures: substituted phenyl with R$^1$, R$^2$; cyclohexadiene; thiophene]

wherein R$^1$ is hydrogen, hydroxy or acetoxy and R$^2$ is hydrogen, chloro or hydroxy when R$^1$ is hydroxy and R$^2$ is hydrogen when R$^1$ is hydrogen or acetoxy;

[thiophene]-CH$_2\overset{O}{\underset{\|}{C}}$-Cl;  (c)

[furan with N-OCH$_3$]-C(=NOCH$_3$)-$\overset{O}{\underset{\|}{C}}$-Cl;  (d)

[4-hydroxy-1,5-naphthyridine]-$\overset{O}{\underset{\|}{C}}$-NH-$\underset{\underset{R}{|}}{CH}$-$\overset{O}{\underset{\|}{C}}$-Cl  (e)

wherein R is phenyl, 4-hydroxyphenyl, 3,4-dihydroxyphenyl or cyclohexa-1,4-dien-1-yl;

$$C_2H_5-N\underset{\diagdown\diagup}{\overset{O\ \ \ O}{\overbrace{N}}}-\overset{O}{\underset{\|}{C}}-NH-\underset{\underset{R}{|}}{CH}-\overset{O}{\underset{\|}{C}}-Cl \quad (f)$$

wherein R is phenyl, 4-hydroxyphenyl, 3,4-dihydroxyphenyl or cyclohexa-1,4-dien-1-yl;

[phenyl]-$\underset{\underset{O-C-H}{\underset{\|}{O}}}{CH}$-$\overset{O}{\underset{\|}{C}}$-Cl;  (g)

[uracil ring]-$\overset{O}{\underset{\|}{C}}$-NH-$\underset{\underset{R}{|}}{CH}$-$\overset{O}{\underset{\|}{C}}$-Cl  (h)

wherein R is phenyl, 4-hydroxyphenyl, 3,4-dihydroxyphenyl or cyclohexadien-1-yl

[pyridazinone with R$^2$]-$\overset{O}{\underset{\|}{C}}$-NH-$\underset{\underset{R^1}{|}}{CH}$-$\overset{O}{\underset{\|}{C}}$-Cl  (i)

wherein R$^1$ is phenyl, 4-hydroxyphenyl, 3,4-dihydroxyphenyl or cyclohexadien-1-yl and R$^2$ is hydrogen or hydroxy;

F$_3$C—S—CH$_2\overset{O}{\underset{\|}{C}}$—Cl;  (j)

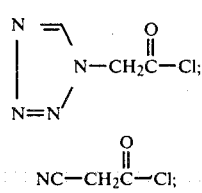 (k)

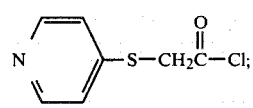 (l)

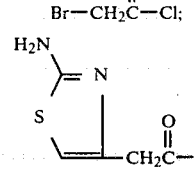 (m)

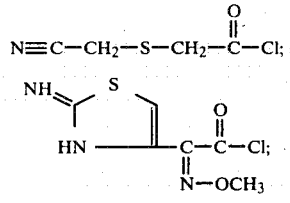 (n)

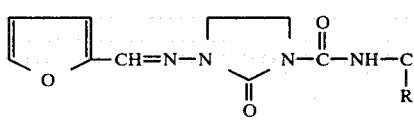 (o)

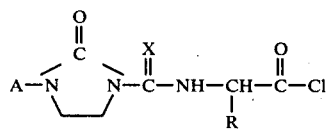 (p)

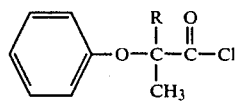 (q)

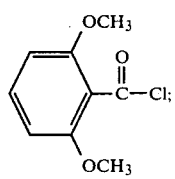 (r)

wherein R is phenyl, 4-hydroxyphenyl, 3,4-dihydroxyphenyl or cyclohexadien-1-yl;

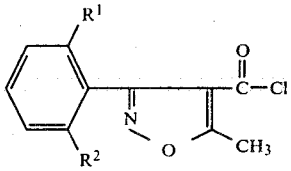 (s)

wherein A is hydrogen or alkyl of 1 to 4 carbon atoms or $CH_3SO_2-$, X is oxygen or sulfur and R is phenyl, 4-hydroxyphenyl, 3,4-dihydroxyphenyl or cyclohexa-1,4-dien-1-yl;

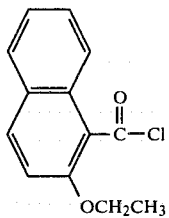 (t)

wherein R is hydrogen or methyl;

(u)

(v)

wherein each of $R^1$ and $R^2$ is hydrogen, chloro or fluoro;

(w)

(x)

wherein $R^1$ is hydrogen, hydroxy or acetoxy and $R^2$ is hydrogen, chloro or hydroxy when $R^1$ is hydroxy and $R^2$ is hydrogen when $R^1$ is hydrogen or acetoxy;

(y)

(z)

(aa)

(bb)

(cc)

(dd) [structure: bicyclic amidine with phenyl-CH₂C(O)Cl]

(ee) B—CH—C(O)—Cl wherein B represents with NH—C(=O)—NHR substituent

[R¹/R² substituted phenyl] or [cyclohexenyl] or [thienyl]

wherein R¹ is hydrogen, hydroxy or acetoxy and R² is hydrogen, chloro or hydroxy when R¹ is hydroxy and R² is hydrogen when R¹ is hydrogen or acetoxy, and R is hydrogen or cyanomethyl;

(ff) [pyrrolidine/pyrroline]—N—CH₂C(O)—Cl (gg) CH₂=CH—CH₂—S—CH₂—C(O)—Cl (hh) [cyclopentyl with C₆H₅]—C(O)—Cl (ii) B—CH—C(O)—Cl wherein B represents with NH—C(=O)—NH—C(=NH)NH₂ substituent

[R¹/R² substituted phenyl] or [cyclohexenyl] or [thienyl]

wherein R¹ is hydrogen, hydroxy or acetoxy and R² is hydrogen, chloro or hydroxy when R¹ is hydroxy and R² is hydrogen when R¹ is hydrogen or acetoxy;

(jj) [phenyl]—CH(—C(O)—Cl)(—O—C(O)—[phenyl-R])
wherein R is hydrogen or methyl (kk) [phenyl]—CH(—C(O)—Cl)(—O—C(O)—[indanyl])

(ll) [1-aminocyclohexyl]—C(O)·Cl and the amino group is blocked, if desired, by conventional blocking groups including particularly by protonation;

(mm) [3,4-dichlorophenyl]—CH(OCH₃)—C(O)—Cl (nn) [4-hydroxyphenyl]—CH(—C(O)—Cl)(—NH—C(=O)—CH₂—NH—C(=O)—NH—C(=NH)NH₂)

(oo) [4-hydroxyphenyl]—CH(—C(O)—Cl)(—NH—C(=O)—NH—[4-hydroxy-1,5-naphthyridinyl])

(pp) (CH₃)₂CHCH₂CH(—C(O)—Cl)(—O—C(O)—[furyl])

(qq) [phenyl]—CH(—C(O)—Cl)(—N(CH₃)—NH₂) as the hydrochloride, if desired (rr) B—CH—C(O)—Cl wherein B represents with NH—C(=O)—[4-oxo-4H-thiopyranyl] substituent

[R¹/R² substituted phenyl] or [cyclohexenyl] or [thienyl]

wherein R¹ is hydrogen, hydroxy or acetoxy and R² is hydrogen, chloro or hydroxy when R¹ is hydroxy and R² is hydrogen when R¹ is hydrogen or acetoxy;

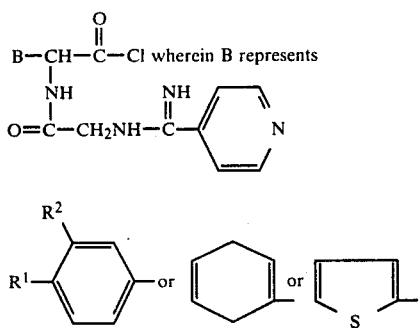

(ss)

wherein $R^1$ is hydrogen, hydroxy or acetoxy and $R^2$ is hydrogen, chloro or hydroxy when $R^1$ is hydroxy and $R^2$ is hydrogen when $R^1$ is hydrogen or acetoxy;

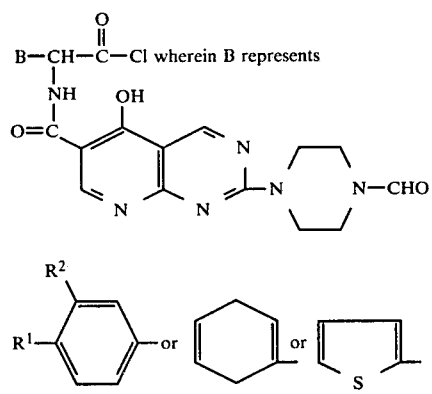

(tt)

wherein $R^1$ is hydrogen, hydroxy or acetoxy and $R^2$ is hydrogen, chloro or hydroxy when $R^1$ is hydroxy and $R^2$ is hydrogen when $R^1$ is hydrogen or acetoxy;

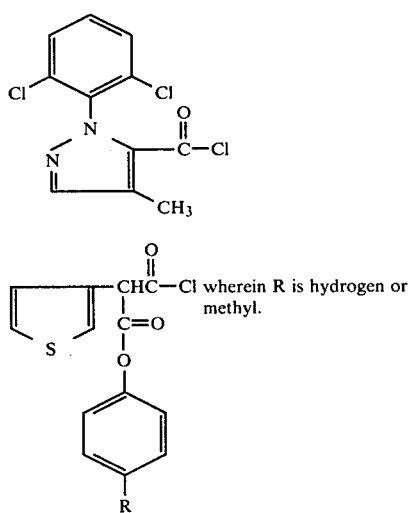

(uu)

(vv)

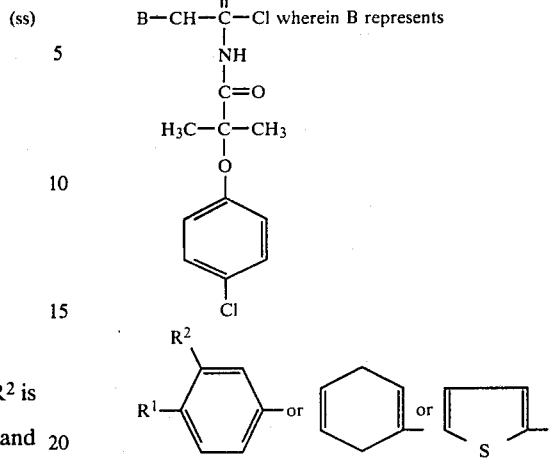

(ww)

wherein $R^1$ is hydrogen, hydroxy or acetoxy and $R^2$ is hydrogen, chloro or hydroxy when $R^1$ is hydroxy and $R^2$ is hydrogen when $R^1$ is hydrogen or acetoxy.

Acid chlorides are normally prepared under vigorous conditions, as by treatment of the acid at reflux with thionyl chloride, but when sensitive groups are present, including sensitive blocking groups, they can be prepared under practically neutral conditions by reaction of a salt of the acid with oxalyl chloride.

DESCRIPTION OF THE PREFERRED EMBODIMENTS

EXAMPLE 1

To a mixture of 6-aminopenicillanic acid (6-APA) and 10 ml. CD$_2$Cl$_2$ and 1.13 ml. trimethylchlorosilane at a temperature of 25°–27° C. there was added dropwise 1.23 ml. triethylamine over a period of thirty minutes. Stirring was continued for an additional two hours. Dry carbon dioxide gas was then bubbled into the mixture for about three hours. At the end of that period NMR (nuclear magnetic resonance) showed the presence of 60% silylated carboxy 6-APA (SCA) having the structure

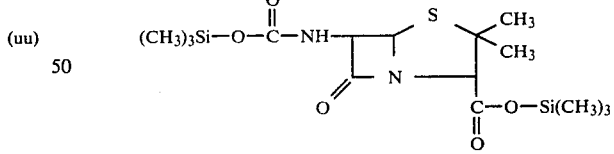

The mixture was held in a refrigerator overnight. The next morning there was added 0.77 ml. N,N-dimethylaniline and the mixture was chilled to −8° C. There was then added 1.2 g. of D-(−)-p-hydroxy-2-phenylglycyl chloride hydrochloride (79% purity) in portions as follows:

| Time in Minutes | Temp. °C. | Grams Added |
|---|---|---|
| Zero | −8 | 0.30 |
| 20 | −4 | 0.30 |
| 40 | −4 | 0.30 |
| 60 | −4 | 0.30 |
| 120 | +8 | |

| Time in Minutes | Temp. °C. | Grams Added |
| --- | --- | --- |
| 220 | +15 | |
| 310 | +20 | |

At the end of the 310 minutes of reaction thin layer chromatography (TLC) performed on a sample of the reaction mixture using a solvent system which was 60% ethyl acetate, 20% acetic acid and 20% water indicated the presence of amoxicillin.

To a cold, 2 ml. sample of the final reaction mixture there was added 1.0 ml. $D_2O$. After separation by centrifugation the aqueous phase was found by NMR to contain 78% amoxicillin and about 20% 6-APA. The presence of amoxicillin was also confirmed by TLC.

EXAMPLE 2

A mixture of 5.4 g. (0.025 mole) 6-aminopenicillanic acid and 6.2 ml. of 93% hexamethyldisilazane (HMDS; 0.0275 mole) and 0.07 g. (about 0.001 mole) imidazole in 40 ml. $CH_2Cl_2$ was refluxed under nitrogen purge for about 17.5 hours. At the end of that period there was added 0.13 ml. (about 0.001 mole) trimethylchlorosilane (TMCS); the solution became turbid. Reflux was continued for an additional 7 hours; deposits of $NH_4Cl$ were noted in the condenser. At that point NMR showed approximately 100% silylation of both the amino and the carboxyl group of the 6-APA. There was then added 0.2 ml. HMDS (0.00125 mole; about 5 mole %) and 0.06 ml. TMCS (about 0.0005 mole) and refluxing with nitrogen purging was continued for an additional 17 hours. At that time the NMR spectrum was the same as before with the addition of small amounts of HMDS and TMCS. Dry carbon dioxide was then bubbled into the reaction mixture at room temperature for 75 minutes; NMR then showed no HMDS and greater than 92% silylated carboxy 6-APA (SCA). There was then added 4.45 ml. N,N-dimethylaniline (DMA)(0.035 mole) and the mixture was chilled to $-3°$ C. Then there was added 5.65 g. D-(−)-2-phenylglycyl chloride (95% purity; 0.026 mole) in portions as follows:

| Time in Minutes | Temp. °C. | Grams Added |
| --- | --- | --- |
| Zero | −3 | 1.05 |
| 20 | 0 | 1.30 |
| 40 | 0 | 1.30 |
| 50 | 0 | 1.00 |
| 60 | 0 | 1.00 |

The reaction was followed by NMR which showed very little change at about 5 hours after the start of the reaction; the temperature was then 3° C. The reaction mixture was then kept packed in ice for the next 16 hours. It was then removed from refrigeration and stirred for 3.5 hours at room temperature (about 20°–24° C.). A large amount of solid material was still present. The reaction mixture was then stirred at room temperature (22°–24° C.) for about 63 hours. At the end of that time there was only slight turbidity. Upon $D_2O$ extraction of a sample NMR showed ampicillin and 6-APA.

The reaction mixture was chilled to about 0° C. and stirred 5 minutes in the cold after the addition of 35 ml. ice water. After polish filtration the mixture was washed with cold water and $CH_2Cl_2$. The aqueous phase, after separation, showed by TLC a large zone slower than ampicillin and 6-APA which represented New Intermediate X. The aqueous phase was adjusted to pH 3.0 with $NH_4OH$ and seeded with ampicillin. Methyl isobutyl ketone (MIBK; 35 ml.) was added and the mixture was stirred, adjusted to pH 5.2 with more $NH_4OH$, stirred at 20° C. for one hour, stirred in an ice-bath for another hour and refrigerated overnight. The precipitate of ampicillin was collected by filtration, washed first with 25 ml. cold water and then with 40 ml. MIBK and finally with 40 ml. of a mixture of 85 parts isopropyl alcohol and 15 parts water, dried at 50° C. and found to weigh 4.5 g. with its identity as ampicillin confirmed by TLC.

EXAMPLE 3

A mixture of 5.4 g. 6-APA, 6.2 ml. HMDS (93%) and 0.06 g. imidazole in 50 ml. $CH_2Cl_2$ was refluxed under nitrogen purge for 18 hours. There was then added 0.1 ml. TMCS which caused turbidity. Reflux for another two hours gave a clear solution with $NH_4Cl$ in the condenser. There was then added another 0.1 ml. TMCS leaving only very slight turbidity. Reflux was continued without nitrogen purge for the next 65 hours. The mixture was then cooled to about 22° C. and dry carbon dioxide addition was begun. After 75 minutes NMR showed the formation of over 90% bis silylated carbamate (SCA). There was then added 4.45 ml. DMA and then 5.6 g. D-(−)-2-phenylglycyl chloride hydrochloride (97% purity) in portions as follows:

| Time in Minutes | Temp. °C. | Grams Added |
| --- | --- | --- |
| Zero | 20 | 1.35 |
| 20 | 20 | 1.30 |
| 32 | 20 | 1.00 |
| 48 | 20 | 1.00 |
| 75 | 20 | 1.00 |

After this mixture had been stirred for an additional 17 hours TLC was run on samples of the reaction mixture and on diluted reaction mixture (1 ml. of reaction mixture with 2 ml. $CH_2Cl_2$) and showed in each a small zone of ampicillin and a large zone of New Intermediate X.

The reaction mixture was then chilled to 0° C., 40 ml. ice water was added and the mixture was stirred 5 minutes, polish filtered and washed with water and with $CH_2Cl_2$. The aqueous phase was separated, 10% was removed for sampling and the remainder was adjusted to pH 3.0 with $NH_4OH$, seeded with ampicillin and stirred. After the addition of 40 ml. more MIBK the mixture was stirred and the pH adjusted to 5.2 with $NH_4OH$ and stirred at room temperature for one hour and then in an ice-bath for another hour. Crystals precipitated. After refrigeration overnight the crystalline product was collected by filtration, washed successively with MIBK, water and MIBK and then 40 ml. isopropanol-water (85-15) and dried at 45° C. to yield 6.25 g. ampicillin (6.8 g. corrected for sampling or a yield of 68%).

EXAMPLE 4

To a mixture of 1.0 g. 6-APA and 1.13 ml. TMCS in 10 ml. $CD_2Cl_2$ there was added dropwise, 1.23 ml. TEA over 30 minutes and the mixture was stirred for an additional two hours. Dry carbon dioxide was then bubbled in for four hours. At that time NMR showed about 55–60% carboxysilylation. The mixture was then held in the refrigerator overnight. In the morning 0.77 ml. DMA was added, the mixture was stirred, chilled to −8° C. and there was added 1.2 g. D-(−)-p-hydroxy-2-phenylglycyl chloride hydrochloride in portions as follows:

| Time in Minutes | Temp. °C. | Grams Added |
|---|---|---|
| Zero | −8 | 0.30 |
| 20 | −4 | 0.30 |
| 40 | −4 | 0.30 |
| 60 | −4 | 0.30 |
| 120 | 8 | |
| 220 | 15 | |
| 310 | 20 | |

At the end of 310 minutes NMR showed about 78% amoxicillin and about 20% 6-APA.

EXAMPLE 5

Dry 6-aminopenicillanic acid (10.0 g., 46.24 mmol., 1.0 eq.) was suspended in anhydrous methylene chloride (175 ml.) with stirring at 25° C. Triethylamine (10.76 g., 106.36 mmol., 2.30 eq.) was added at 25° C. followed by the addition of trimethylchlorosilane (11.70 g., 107.75 mmol., 2.33 eq.) over a 10–15 minute period maintaining the temperature below about 32° C. by the rate of addition of trimethylchlorosilane. After stirring for 20–30 minutes the mixture containing precipitated triethylamine hydrochloride was analyzed for complete silylation by 80 MHz NMR. The mixture was then gassed with carbon dioxide at 20° C. for about 2 hours and analyzed for complete carboxylation by 80 MHz NMR. Further gassing was sometimes necessary. The volume of the carboxylation mix was readjusted if necessary to about 175 ml. with dry methylene chloride. After carboxylation was complete the slurry was treated with propylene oxide (2.95 g., 3.56 ml., 50.87 mmol., 1.1 eq.) and cooled to 0°–5° C. D-(−)-2-(p-Hydroxyphenyl)glycyl chloride hydrochloride hemidioxane solvent was added in 5×2.71 g. portions at about 2° C. [a total of 13.54 g. (50.87 mmol., 1.1 eq.) was added]. Each portion of acid chloride was allowed to dissolve* before the next portion was added. This required about 20 minutes per portion. This portionwise addition was very important. The final acylation mix was examined for any undissolved acid chloride hydrochloride. The mix was held at 0°–5° C. for 30 minutes and treated with cold (0°–5° C.) deionized (DI) water (100 mls.) with high speed agitation for 10 minutes. The mix was allowed to separate and the lower phase methylene chloride was removed. The rich aqueous mix was polish filtered (very little solid) through a thin (Dicalite) precoat of diatomaceous earth and the cake was washed with cold (0°–5° C.) DI water (15 mls.). Any lower phase organic layer was removed prior to crystallization. The clear, light-yellow aqueous solution (pH 2–2.5) was adjusted to pH 3.5 at 0°–5° C. and seeded if necessary. The slurry was held at 0°–5° C. for 40 minutes and the pH adjusted to 4.8–5.0 with 6 N ammonium hydroxide and crystallized for 2 hours. The slurry was filtered and the solid amoxicillin thus collected was washed with a mixture of cold (0°–5° C.) 1:1 isopropanol/water and the cake was washed with methylene chloride (30 ml.) giving about 13.5 g. (about 70%) of snow-white amoxicillin trihydrate.

*Stirring was stopped and the mixture examined for any solid at the bottom of the flask. Do not warm up slurry above 5° C. for this test or results will be erroneous.

EXAMPLE 6

6-Aminopenicillanic acid (108 g.; 0.5 mole), 1.0 g. imidazole (0.017 mole), 800 ml. dry methylene chloride and 120 ml. (0.56 mole) of HMDS (about 98% purity) was stirred and heated at reflux for 3.3 hours. The reaction was purged with dry nitrogen gas throughout the reflux to sweep out the $NH_3$ formed in the reaction. Then 2.0 ml. of trimethylchlorosilane (TMCS) was added (0.016 mole). Reflux continued with $N_2$ purging for an additional 19 hours and then the $NH_4Cl$ sublimed in the condenser was cleared out and 2.6 ml. TMCS (0.0206 mole) was added to the reaction. Reflux with $N_2$ purging was continued for another 34 hours. The volume in the reaction mix was brought to 1000 ml. with dry methylene chloride. The NMR then showed 100% silylation of the amino and carboxyl group on the 6-aminopenicillanic acid. The solution was blanketed with $N_2$ gas and held for nine days. NMR confirmed the above and stability. The solution was stirred and $CO_2$ was bubbled in for about 90 minutes. Temperature 20°–22° C. NMR showed 100% conversion of the bis trimethylsily 6-aminopenicillanic acid to the bis trimethylsilylcarboxy 6-aminopenicillanic acid (SCA).

This master mix was used for the acylation experiments described below. The chemical in this solution had the formula

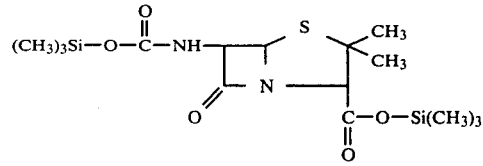

NMR showed the bis trimethylsilylcarboxy 6-aminopenicillanic acid stable after nine days.

100 ml. of master mix (SCA equivalent to 10.8 g. 6-aminopenicillanic acid; 0.05 mole) was stirred at 22° C. and 8.0 g. TEA.HCl (0.058 mole) and 4.2 ml. of propylene oxide (0.06 mole) (See U.S. Pat. No. 3,741,959) was added. Some TEA.HCl precipitated. The mix was stirred and chilled to +3° C. 15.5 g. of D-(−)-p-hydroxyphenylglycylchloride hydrochloride hemidioxane solvate (79% purity; 0.055 mole) was added to the reaction in portions as follows:

| Grams Added | Time in Minutes | Temp. °C. |
|---|---|---|
| 3.0 | Zero | +3° |
| 3.0 | 7 | +2° |
| 3.0 | 20 | +2° |
| 6.5 | 33 | +2° |
| 15.5 | | |

After another seventy minutes about 50 ml. of dry methylene chloride was added to the reaction mixture to reduce the viscosity.

After another 160 minutes a 2 ml. sample was removed and added to 1.0 ml. $D_2O$. After centrifugation NMR analysis of the aqueous phase indicated about 6% unacylated 6-aminopenicillanic acid.

Ten minutes later the reaction mixture was transferred to a 600 ml. beaker and the transfer completed with 50 ml. methylene chloride wash. While stirring in an ice bath there was added 60 ml. cold deionized ice water to provide a solution of two phases containing no solids and having pH 1.0.

15.0 ml. liquid anion exchange resin ("LA-1") was added to the two phase system with stirring and seeding at pH 2.0. Crystallization began. An additional 10.0 ml. LA-1 was added slowly over about 5 minutes. The pH was 3.0. There was then added 0.15 g. NaBH$_4$. Then there was added 5.0 ml. LA-1; the pH was 4.5. Stirring was continued and there was added 1.0 g. NaHSO$_3$ (sodium bisulfite) in 4.0 ml. water dropwise. There was then added 10.0 ml. LA-1; the pH continued to rise. Total LA-1 40 ml., final pH was 5.6. There was then added 5 ml. acetone. At this point 1.5 g. NaHSO$_3$ dissolved in 6.0 ml. water was added over 30 minutes. Stirring in the ice bath was continued. The precipitated product was collected by filtration and the cake washed successively with 50 ml. methylene chloride, 40 ml. water, 100 ml. isopropyl alcohol-water (80:20) and 100 ml. methylene chloride. The cake was then dried at atmospheric pressure and 45° C. to yield 18.2 g. of amoxicillin trihydrate which was a yield of 87% based on 6-aminopenicillanic acid; correcting for 1% sampling, the overall yield was about 88%.

"LA-1" liquid anion exchange resin is a mixture of secondary amines wherein each secondary amine has the formula

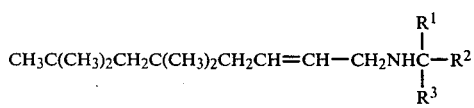

wherein each of $R^1$, $R^2$ and $R^3$ is an aliphatic hydrocarbon radical and wherein $R^1$, $R^2$ and $R^3$ contain in the aggregate from 11 to 14 carbon atoms; this particular mixture of secondary amines which is sometimes referred to as "Liquid Amine Mixture No. I," is a clear amber liquid having the following physical characteristics: viscosity at 25° C. of 70 cps.; specific gravity at 20° C. of 0.845; refractive index at 25° C. of 1.467; distillation range at 10 mm.: up to 160° C.—4%, 160° to 210° C.—5%, 210° to 220° C.—74%, above 220° C.—17%.

EXAMPLE 7

A methylene chloride solution (5.0 mls.) of trimethylsilyl 6-trimethylsilyloxycarbonylaminopenicillanate (0.54 g., 2.497 mmol.) was treated with triethylamine hydrochloride (0.20 g., 1.45 mmol.) followed by propylene oxide (0.162 g., 2.75 mmol.) at 25° C. The mixture was stirred at 25° C. for 20 minutes to facilitate the solution of most of the triethylamine hydrochloride. Phenoxyacetyl chloride (0.43 g., 2.75 mmol.) was added dropwise at 25° C. and the mixture stirred at 25° C. for 30 minutes. A sample was removed and analyzed by CMR at 20.0 MHz. CMR (carbon-13 nuclear magnetic resonance spectroscopy) data showed the complete disappearance of phenoxyacetyl chloride and the APA carbamate and the appearance of penicillin V trimethylsilyl ester. The presence of penicillin V trimethylsilyl ester was proved by spectral comparison with an identical sample prepared by silylation of penicillin V free acid with triethylamine and trimethylchlorosilane. The yield estimated from the CMR spectrum was 85 to 90%.

Similarly prepared using the same molar quantities of reagents and the appropriate acid chloride were cloxacillin, dicloxacillin, staphcillin and nafcillin. CMR data on these acylation mixes showed an extremely clean acylation mix with yields estimated to be at least 85%.

EXAMPLE 8

Reaction according to the above procedures of a compound having the formula

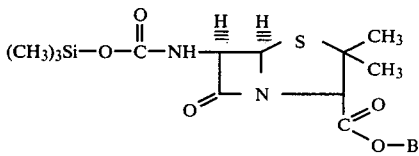

wherein B is an easily cleavable ester protecting group selected from the group consisting of trimethylsilyl, benzhydryl, benzyl, p-nitrobenzyl, p-methoxybenzyl, trichloroethyl, phenacyl, acetonyl, methoxymethyl, 5-indanyl, 3-phthalidyl, 1-[(ethoxycarbonyl)oxy]ethyl, pivaloyloxymethyl and acetoxymethyl with a reagent which is the appropriate acid chloride or acid chloride hydrochloride, said reagent containing blocking groups as necessary, followed by removal of any blocking groups whose removal is desired produces the following compounds: almecillin; armecillin, azidocillin; azlocillin; bacampicillin; Bay K 4999 having the formula

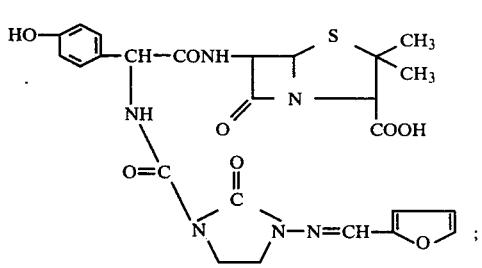

BL-P1654 having the formula

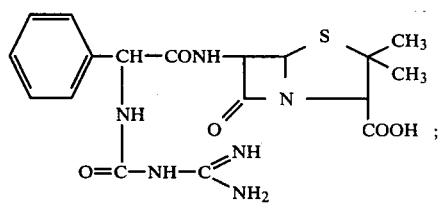

BL-P1908 having the formula

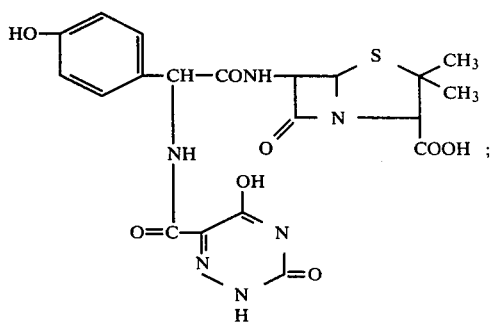

carfecillin; carindacillin; cyclacillin; clometocillin; cloxacillin; dicloxacillin; EMD-32412 having the formula

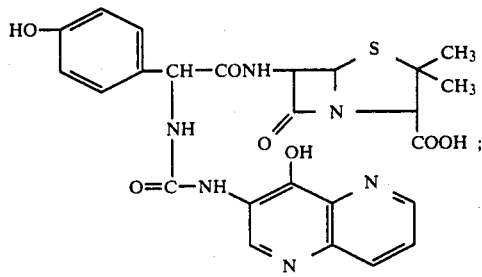

epicillin, floxacillin (flucloxacillin); furbucillin; hetacillin; I.S.F.-2664 having the formula

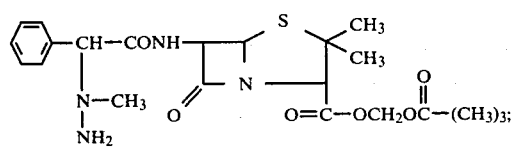

isopropicillin; methicillin; mezlocillin; nafcillin; oxacillin; phenbenicillin; PC-455 having the formula

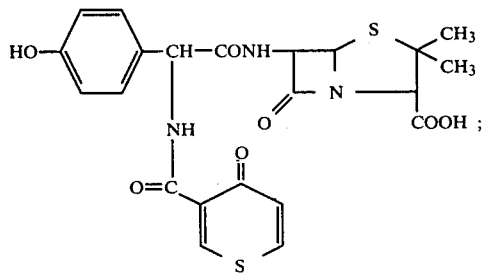

aparcillin (PC-904) having the formula

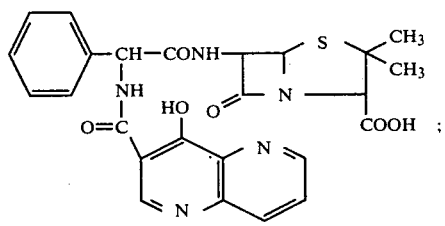

piperacillin; 3,4-dihydroxypiperacillin; pirbenicillin; pivampicillin; PL-385 having the formula

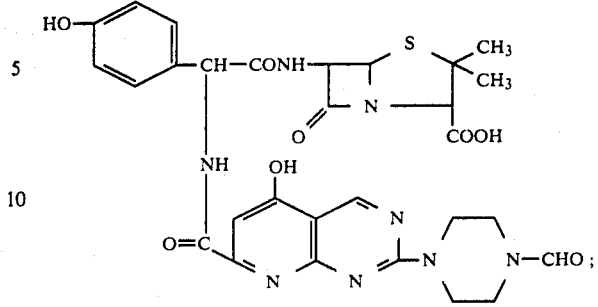

prazocillin; sarmoxicillin; sarpicillin; ticarcillin cresyl sodium; ticarcillin; carbenicillin; carfecillin; fibracillin and Bay-e-6905 having the formula

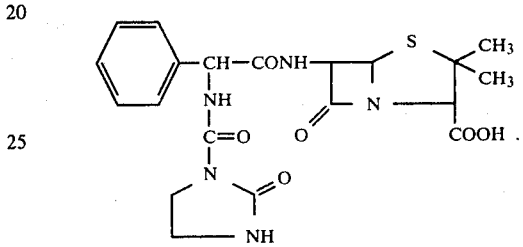

This invention is capable of industrial application.
We claim:
1. A compound having the formula

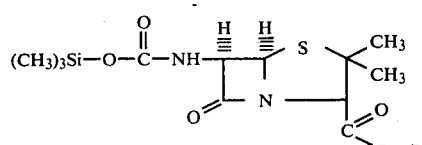

wherein B is an easily cleavable ester protecting group.
2. A compound having the formula

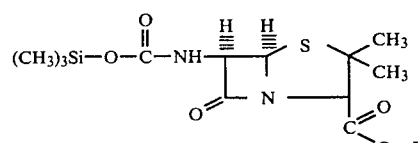

wherein B is an easily cleavable ester protecting group selected from the group consisting of trimethylsilyl, benzhydryl, benzyl, p-nitrobenzyl, p-methoxybenzyl, trichloroethyl, phenacyl, acetonyl, methoxymethyl, 5-indanyl, 3-phthalidyl, 1-[(ethoxycarbonyl)oxy]ethyl, pivaloyloxymethyl and acetoxymethyl.
3. The compound having the formula

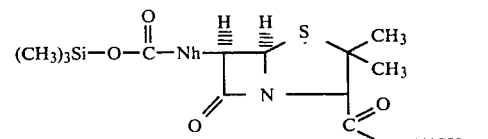

4. The compound of claim 2 having the formula

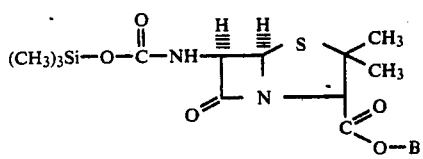
wherein B is 5-indanyl.
5. The compound of claim 2 having the formula
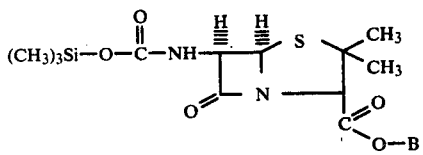
wherein B is 3-phthalidyl.
6. The compound of claim 2 having the formula
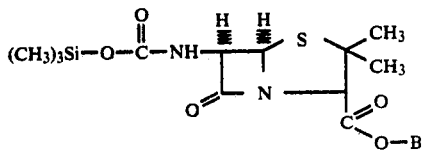
wherein B is 1-[(ethoxycarbonyl)oxy]ethyl.
7. The compound of claim 2 having the formula
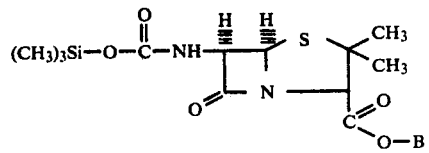
wherein B is pivaloyloxymethyl.
8. The compound of claim 2 having the formula
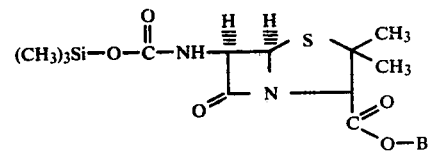
wherein B is acetoxymethyl.
* * * * *